(12) United States Patent
Seal et al.

(10) Patent No.: US 7,594,728 B2
(45) Date of Patent: Sep. 29, 2009

(54) ADJUSTABLE DEVICE FOR VISION TESTING AND THERAPY

(75) Inventors: Jim Seal, South Boca Raton, FL (US); Sigrid Kenkel, Boca Raton, FL (US); Michelle Boster, Boca Raton, FL (US); Patrick J. Paul, Downington, PA (US)

(73) Assignee: NovaVision, Inc., Boca Raton, FL (US)

( * ) Notice: Subject to any disclaimer, the term of this patent is extended or adjusted under 35 U.S.C. 154(b) by 119 days.

(21) Appl. No.: 11/640,548

(22) Filed: Dec. 18, 2006

(65) Prior Publication Data

US 2007/0171372 A1 Jul. 26, 2007

Related U.S. Application Data

(60) Provisional application No. 60/750,867, filed on Dec. 16, 2005.

(51) Int. Cl.
*A61B 3/14* (2006.01)
*A61B 3/10* (2006.01)

(52) U.S. Cl. ................................ 351/210; 351/205

(58) Field of Classification Search ......... 351/205–206, 351/210, 221, 245–246
See application file for complete search history.

(56) References Cited

U.S. PATENT DOCUMENTS

| | | | | |
|---|---|---|---|---|
| 1,463,847 A * | 8/1923 | Shilling | ........... | 27/25.1 |
| 2,213,484 A | 9/1940 | Briggs | ........... | 128/76.5 |
| 3,883,234 A | 5/1975 | Lynn et al. | ........... | 351/23 |
| 4,260,227 A | 4/1981 | Munnerlyn et al. | ........... | 351/24 |
| 4,408,846 A | 10/1983 | Balliet | ........... | 351/203 |
| 4,429,961 A | 2/1984 | Sheingorn | ........... | 351/226 |
| 4,533,221 A | 8/1985 | Trachtman | ........... | 351/203 |
| 4,660,945 A | 4/1987 | Trachtman | ........... | 351/203 |

(Continued)

FOREIGN PATENT DOCUMENTS

DE 9305147 4/1994

(Continued)

OTHER PUBLICATIONS

Portable Tech/Emory Device Checks for Concussions, http://www.gatech.edu/news-room/release.php?id=554, Apr. 26, 2005.

(Continued)

*Primary Examiner*—Scott J Sugarman
*Assistant Examiner*—Dawayne A Pinkney
(74) *Attorney, Agent, or Firm*—Sunstein Kann Murphy & Timbers LLP

(57) ABSTRACT

An adjustable and foldable device for visual field testing or treatment includes a computer display mounted on a base and presents visual stimuli to the patient. An associated head support assembly with a chinrest supports and positions the head of the subject with respect to the display. An articulated arm joins the base and the head support assembly. The arm will resist a given downward force supplied by the head, and is foldable toward the display to create a more compact and portable device. Additional articulations may allow the head support assembly to fold upon arm, and the arm to fold upon the base. The device may include a locking mechanism that secures the device in a folded or unfolded configuration.

32 Claims, 6 Drawing Sheets

U.S. PATENT DOCUMENTS

| | | | |
|---|---|---|---|
| 4,679,920 A | 7/1987 | Takashi et al. | 351/226 |
| 4,971,434 A | 11/1990 | Ball | 351/224 |
| 4,995,717 A | 2/1991 | Damato | 351/224 |
| 5,050,982 A | 9/1991 | Meissner | 351/203 |
| 5,088,810 A | 2/1992 | Galanter et al. | 351/203 |
| 5,139,323 A | 8/1992 | Schillo | 351/45 |
| 5,147,284 A | 9/1992 | Fedorov et al. | 600/9 |
| 5,191,367 A | 3/1993 | Salibello et al. | 351/243 |
| 5,206,671 A | 4/1993 | Eydelman et al. | 351/203 |
| 5,241,332 A | 8/1993 | Farrell | 351/246 |
| 5,305,027 A | 4/1994 | Patterson | 351/44 |
| 5,321,445 A | 6/1994 | Fossetti | 351/203 |
| 5,325,136 A | 6/1994 | Salibello et al. | 351/243 |
| 5,363,154 A | 11/1994 | Galanter et al. | 351/203 |
| 5,455,643 A | 10/1995 | Ki-Ho | 351/203 |
| 5,534,953 A | 7/1996 | Schmielau | 351/203 |
| 5,539,481 A | 7/1996 | Vax | 351/203 |
| 5,539,482 A | 7/1996 | James et al. | 351/246 |
| 5,550,602 A | 8/1996 | Braeuning | 351/243 |
| 5,565,949 A | 10/1996 | Kasha, Jr. | 351/224 |
| 5,883,692 A | 3/1999 | Agonis et al. | 351/224 |
| 5,912,723 A | 6/1999 | Maddess | 351/246 |
| 5,946,075 A | 8/1999 | Horn | 351/246 |
| 5,991,085 A | 11/1999 | Rallison et al. | 359/630 |
| 6,062,687 A | 5/2000 | Lofgren-Nisser | 351/46 |
| 6,286,960 B1 | 9/2001 | Tomita | 351/245 |
| 6,321,338 B1 | 11/2001 | Porras et al. | 713/201 |
| 6,359,601 B1 | 3/2002 | Maguire, Jr. | 345/7 |
| 6,364,486 B1 | 4/2002 | Ball et al. | 351/203 |
| 6,386,706 B1 | 5/2002 | McClure et al. | 351/237 |
| 6,406,437 B1 | 6/2002 | Zur et al. | 600/558 |
| 6,431,708 B2 | 8/2002 | Krebs | 351/203 |
| 6,443,977 B1 | 9/2002 | Jaillet | 607/88 |
| 6,464,356 B1 | 10/2002 | Sabel et al. | 351/203 |
| 6,519,703 B1 | 2/2003 | Joyce | 713/201 |
| 6,540,355 B1 | 4/2003 | Couture | 351/203 |
| 6,592,221 B1 | 7/2003 | Stregova | 351/203 |
| 6,742,892 B2 | 6/2004 | Liberman | 351/203 |
| 6,990,377 B2 | 1/2006 | Gliner et al. | 607/54 |
| 7,004,912 B2 | 2/2006 | Polat | 600/558 |
| 7,104,659 B2 | 9/2006 | Grier et al. | 359/614 |
| 7,309,128 B2 * | 12/2007 | Cappo et al. | 351/224 |
| 2002/0047987 A1 | 4/2002 | Massengill et al. | 351/204 |
| 2002/0107960 A1 | 8/2002 | Wetherall et al. | 709/225 |
| 2003/0090439 A1 | 5/2003 | Spitzer et al. | 345/8 |
| 2003/0156254 A1 | 8/2003 | Turovetsky | 351/203 |
| 2003/0214630 A1 | 11/2003 | Winterbotham | 351/203 |
| 2004/0012758 A1 | 1/2004 | Lin | 351/203 |
| 2004/0051848 A1 | 3/2004 | Gotze et al. | 351/203 |
| 2004/0075811 A1 | 4/2004 | Liberman | 351/203 |
| 2004/0100616 A1 | 5/2004 | Eremeev | 351/203 |
| 2004/0257528 A1 | 12/2004 | Miyake et al. | 351/203 |
| 2005/0001980 A1 | 1/2005 | Spector | 351/203 |
| 2005/0041208 A1 | 2/2005 | Winterbotham | 351/203 |
| 2005/0213033 A1 | 9/2005 | Sabel | 351/203 |
| 2005/0213034 A1 | 9/2005 | Nagayoshi | 351/203 |
| 2005/0213035 A1 | 9/2005 | Yoshimeki et al. | 351/203 |
| 2006/0092377 A1* | 5/2006 | Todd et al. | 351/246 |
| 2006/0283466 A1 | 12/2006 | Sabel | 128/898 |
| 2006/0288258 A1* | 12/2006 | Lo et al. | 714/46 |
| 2006/0290885 A1 | 12/2006 | Covannon et al. | 351/212 |
| 2007/0038142 A1 | 2/2007 | Todd et al. | 600/558 |
| 2007/0171372 A1 | 7/2007 | Seal et al. | 351/245 |

FOREIGN PATENT DOCUMENTS

| | | |
|---|---|---|
| DE | 10207839 | 9/2002 |
| EP | 115263 | 8/1984 |
| EP | 128783 | 12/1984 |
| EP | 135736 | 8/1985 |
| EP | 0242723 | 10/1987 |
| EP | 0537945 A1 | 4/1993 |
| EP | 544631 | 6/1993 |
| EP | 689822 | 1/1996 |
| EP | 775464 | 5/1997 |
| EP | 830839 | 3/1998 |
| EP | 1186271 | 3/2002 |
| EP | 1236432 | 9/2002 |
| EP | 1236433 | 9/2002 |
| EP | 1384462 | 1/2004 |
| EP | 1402869 | 3/2004 |
| EP | 1403680 A1 | 3/2004 |
| GB | 1465561 | 2/1977 |
| WO | WO 8000405 | 3/1980 |
| WO | WO 8810088 | 12/1988 |
| WO | WO 9100553 | 1/1991 |
| WO | WO 9110393 | 7/1991 |
| WO | WO 9200037 | 1/1992 |
| WO | WO 9517227 | 6/1995 |
| WO | WO 9700653 | 1/1997 |
| WO | WO 9811819 | 3/1998 |
| WO | WO 9849992 | 11/1998 |
| WO | WO 9952419 | 10/1999 |
| WO | WO 9959461 | 11/1999 |
| WO | WO 0012042 | 3/2000 |
| WO | WO 0036971 | 6/2000 |
| WO | WO 0113859 | 3/2001 |
| WO | WO 0145630 | 6/2001 |
| WO | WO 0147463 | 7/2001 |
| WO | WO 0180808 | 11/2001 |
| WO | WO 0209578 | 2/2002 |
| WO | WO02/39754 | 5/2002 |
| WO | WO 02053072 | 7/2002 |
| WO | WO 03002070 | 1/2003 |
| WO | WO 03002190 | 1/2003 |
| WO | WO 03007944 | 1/2003 |
| WO | WO 03020195 | 3/2003 |
| WO | WO 03041630 | 5/2003 |
| WO | WO 03065964 | 8/2003 |
| WO | WO 03092482 | 11/2003 |
| WO | WO 03092570 | 11/2003 |
| WO | WO 03098529 | 11/2003 |
| WO | WO 2004066900 | 8/2004 |
| WO | WO 2005004985 | 1/2005 |
| WO | WO 2005037177 | 4/2005 |
| WO | WO 2005044096 | 5/2005 |
| WO | WO 2005063153 | 7/2005 |
| WO | WO 2005092270 | 10/2005 |
| WO | WO 2005110326 | 11/2005 |
| WO | WO 2005122872 | 12/2005 |
| WO | WO2006/002070 | 1/2006 |
| WO | WO 2006006563 | 1/2006 |
| WO | WO 2007109724 | 9/2007 |

OTHER PUBLICATIONS

Erich Kasten et al., Computer-based training for the treatment of partial blindness, Nature Medicine, vol. 4, No. 9, p. 1083-1087, Sep. 1998.

Burkhard Pleger et al., Functional magnetic resonance imaging mirrors recovery of visual perception after repetitive tachistoscopic stimulation in patients with partial cortical blindness, Neuroscience Letters, vol. 335, p. 192-194, 2003.

Walter Widdig et al., Repetitive visual stimulation: A neuropsychological approach to the treatment of cortical blindness, NeuroRehabilitation, vol. 18, p. 227-237, 2003.

Robert Sekuler, Vision Loss in an Aging Society: A Multidisciplinary Perspective/Vision Rehabilitation: Assessment, Intervention and Outcomes/The Lighthouse Handbook on Vision; Aug. 1, 2001, Gerontologist 556, vol. 41, Issue 4; ISSN: 0016-9013, © 2001.

Erich Kasten, Dorothe A. Poggel, Bernhard A. Sabel, Computer Based Training Stimulus Detection Improves Color and Simple Pattern Recognition in the Defective Field of Hemianopic Subjects; Nov. 1, 2000, Journal of Cognitive Neuroscience 1001, ISSN: 0898-929X; vol. 12, Issue 6; © 2000.

Rewiring Your Gray Matter: The brain: You can trach an old brain new tricks. Neuroplasticity promises to give a whole new meaning to 'changing your mind'; Jan. 1, 2000, Newsweek 63; ISSN: 0028-9604; vol. 134, Issue 26, © 2000.

Teaching the brain to restore sight; Popular Mechanics, Jan. 18, 1999, Associated Press Newswires, © 1999.

Philip A. Schwartzkroin, Synaptic Plasticity; Molecular, Cellular, and Functional Aspects (book reviews); May 20, 1994, Science 1179; vol. 264, No. 5162, ISSN: 0036-8075; © 1994.

J. Zihl, et al., Restitution of visual function in patients with cerebral blindness; Zihl and von Cramon, J Neurol Neurosurg Psychiatry (1979).

J. Zihl, et al., Restitution of visual field in patients with damage to the geniculostriate visual pathway; Zihl and von Cramon, Human Neurobiology (1982).

E. Kasten, S. Wuest, B. Sabel, Journal of Clinical and Experimental Neuropsychology 1998, vol. 20, No. 5, pp. 581-598 "Residual Vision in Transition Zones in Patients with Cerebral Blindness".

F. Schmielau, Restitution of visual function in cases of brain damaged patients: Efficacy of localization specific sensory and sensomotoric rehabilitation procedures. In "Psychologie in der Neurologie" [Psychology in Neurology], P. Jacobi (editor). Berlin: Springer, 115-126(1989).

E. Kasten et al., Restoration of vision II: Residual functions and training-induced visual field enlargement in brain-damaged patients.

K.K. ball, et al, Journal of the Optical Society of America A, vol. 5, No. 12, pp. 2210-2219 "Age and Visual Search: Expanding the Useful Field of View", Dec. 1998.

E. Kasten, et al., Spatial Vision, vol. 10, No. 4, pp. 499-503, "Programs for Diagnosis and Therapy of Visual Field Deficits in Vision Rehabilitation", 1997.

E. Kasten, et al., Restorative Neurology and Neurology and Neuroscience, vol. 8, No. 3, pp. 113-127, "Visual Field Enlargement After Computer Training in Bran-damaged Patients Whit Homonymous Deficits: An Open Pilot Trial", Aug. 1995.

Alan Cowley, Alan Cowley, Perimetric Study of Field Defects in Monkeys After Cortical and Retinal Ablations, Quarterly Journal of Experimental Psychology, pp. 232-245, Dec. 18, 1967.

New Research on the Efficacy of NoveVision VRT Presented at 32nd Annual North American Neuro-Ophthalmology Society Meeting; Mar. 2, 2006, Business Wire © 2006.

Sharon Begley, Training the brain to see again; Sharon Begley, May 1, 2005, Saturday Evening Post, vol. 277; Issue 3; ISSN: 00489239; © 2005 Bell & Howell Information and Learning Company.

In-Sung Yoo, Advances in Medicine: New therapy gives hope to stroke victims; In-Sung Yoo, Mar. 1, 2005, The New Journal, © 2005, The New Journal.

Sharon Begley, Stroke patients have hope in sight; As part of the revolution in neurobiology, doctors are trying to train healthy brain cells to take over the visual function of neurons damaged by a stroke; Sharon Begley, Wall Street Journal, Feb. 4, 2005, The Globe and Mail.

John Dorschner, Stroke victims improve vision with computer therapy; John Dorschner, Knight Ridder Newspapers, Jul. 19, 2004, The Tallahassee Democrat, © 2004.

Sharon Begley, Survival of the Busiest—Parts of the Brain That Get Most Use Literally Expand And Rewire on Demand; Sharon Begley, Oct. 11, 2002, The Wall Street Journal, © 2002.

Patienteninformation Sehtherapie, Spectros, Nethera, http://www.teltra.org/cms/site/index.php?id=29, 2005.

Patienteninformation Sehtherapie, Otcb, Nethera, http://www.teltra.org/cms/site/index.php?id=11, 2005.

Spectros Technik/Ablauf, Nethera, Teltra, http://www.teltra.org/cms/site/index.php?id=77, 2005.

International Search Report.

Patent Cooperation Treaty, *International Preliminary Report on Patentability*, International Application No. PCT/EP2007/001741; Date of Issuance Jun. 18, 2008 (Switzerland).

Dr. Kloss, "National Academy of Mortuary Science", Retrieved on Dec. 15, 2008; pp. 1-9. http://www.drkloss.com/samplelesson.html.

* cited by examiner

ADJUSTABLE DEVICE FOR VISION TESTING AND THERAPY

TECHNICAL FIELD

The present invention relates to systems and methods to provide visual field of view characterization (diagnostic) and vision restoration therapy to subjects including patients with vision impairment. In particular, the invention is directed toward positioning users and a source of visual stimuli to ensure accurate diagnostic testing and therapy.

BACKGROUND

Stimulating the vision system of a subject with vision impairments may improve their visual performance of patients. For example, as documented in U.S. Pat. No. 6,464,356, and US Published Patent Application No. 2005/0213033, which are hereby incorporated by reference herein in their entirety, presenting visual stimuli to the areas of a human's visual system may allow improvement in the user's vision. Such a procedure may be carried out on a personal computer for home use, the therapy performed in sessions on a daily schedule for a set period of time (e.g., an hour).

The location and orientation of a user's head relative to a display, used to present visual stimuli, needs to be identified each time therapy is performed to properly stimulate the correct zones in a user's visual field. Previous therapeutic regimens relied upon a user fixing their gaze in a particular location. The natural tendency of persons to move after being in an unsupported, fixed position for a relatively long period of time may cause misalignment of the visual stimuli relative to a user's visual field. Such misalignment may limit the effectiveness of a therapeutic session. Even if a user attempts to remain stationary relative to a display, identifying the proper position may be difficult, especially for individual users outside of a clinical setting. In addition, the amount of time required to properly align the relative position of the display with a user's visual field can be substantial.

Because devices for visual field testing and therapy tend to be bulky, they are typically used in dedicated facilities. However, it may be inconvenient to transport a patient to such a facility. It may therefore be desirable to use such a device in non-dedicated facilities such as a home, rehabilitation center, or hospital room. Additionally, positional adjustment of the subject relative to the source of stimulus may be overly time consuming or difficult.

SUMMARY OF THE INVENTION

In illustrative embodiments of the present invention, an adjustable device provides visual testing or treatment to a subject. The device has a computer display mounted on a base. A head support assembly includes a chinrest and aids in the positioning of the head of a subject with respect to the display. The head support assembly is joined to the base, and thus to the display, via an articulated arm. The chinrest will resist a given downward force of the head. During transport, the head support assembly is foldable toward the display to create a more compact and portable device.

In related embodiments, the chinrest and display may be adjustable in multiple ways. For example, the elevation of the chinrest relative to the fixation center of the display may be adjustable. The lateral position of the chinrest may be adjustable. The elevation of the chinrest and the elevation of the display may be adjustable with respect to the base, and may be adjusted simultaneously to maintain their relative elevations, while adjusting the absolute elevation to conform with a subject's height or comfort. The positions of the chinrest and display may be adjusted manually. The positions may also be adjusted automatically. For example, an eye-tracker can be used to determine the best position for the chinrest relative to the display and the device can use that information to adjust the position of the chinrest and/or display. In embodiments, positioning of the chinrest and display can be done manually, or electromechanically. A memory storage device may be used to store positional information associated with a given subject. In response to an input of information identifying the subject, the device may then automatically adjust to reproduce the stored positional settings associated with the subject.

In a further embodiment, in order to increase the safety of operating the device, the chinrest supports the head of the subject by supplying only a limited upward, countering force. Application of a force in excess of a threshold force value will cause the downward collapse of the chinrest. As a result, the device is less likely to be toppled.

In further related embodiments, a computer may be integrated into the device or otherwise operatively coupled to the device via wired or wireless (e.g., radio frequency) connections. The computer directs the presentation of stimuli and records user responses to the stimuli. A variety of input devices may be used, including a mouth-actuated switch, a microphone, a finger actuated switch, a foot actuated switch, a joystick, a mouse, a trackpad, a trackball, and an accelerometer-based device.

In a yet another embodiment, the head support assembly includes a sensor that is operatively coupled to the computer and detects the presence of the head of a subject. As a result, the computer will compensate for the so-detected presence or absence of the subject and thereby avoid the accumulation of spurious data from a non-present subject. For example, the removal of the subject's head may trigger a pause condition and the detected return of the patient's head may trigger a resumption of a program of visual testing or therapy.

In other embodiments, the device may include antiglare components such as an antiglare hood or a glare detector. For ease of portability, the device may have a handle attached to the display.

In further embodiments, a device for administering testing or therapy procedures includes a display that is foldably connected to a base and has a head support assembly that is foldably connected to the display via an articulated arm The head support assembly may also be foldably connected to the arm. The device may be lockable is a folded and/or unfolded state. An actuator may be used to lock and/or unlock the device in order to switch configurations between a folded and unfolded mode.

BRIEF DESCRIPTION OF THE DRAWINGS

The foregoing features of the invention will be more readily understood by reference to the following detailed description, taken with reference to the accompanying drawings, in which.

DETAILED DESCRIPTION

Illustrative embodiments of the invention described herein are directed toward devices and methods to evaluate and to treat a subject (i.e., a patient) to compensate for impairment of vision. A display presents visual stimuli that are viewed by the subject, the stimuli resulting in evaluation and/or treatment of the impaired vision of the subject. Embodiments provide a device that has a positionable head support assembly that includes a chinrest and supports the head of a subject relative to a display so that the subject's visual field can be precisely stimulated for visual field testing or therapy. Embodiments include features that allow the device facilitate adjustment, and make the device safer and more convenient to use, including features that allow the device to be folded for ease of transport. As a result, the device is well suited to use at a non-dedicated clinical setting such as a hospital room, doctor's office or the home of a subject. A padded case may be provided to pack the folded device in for secure shipping or carrying.

Figure 1:
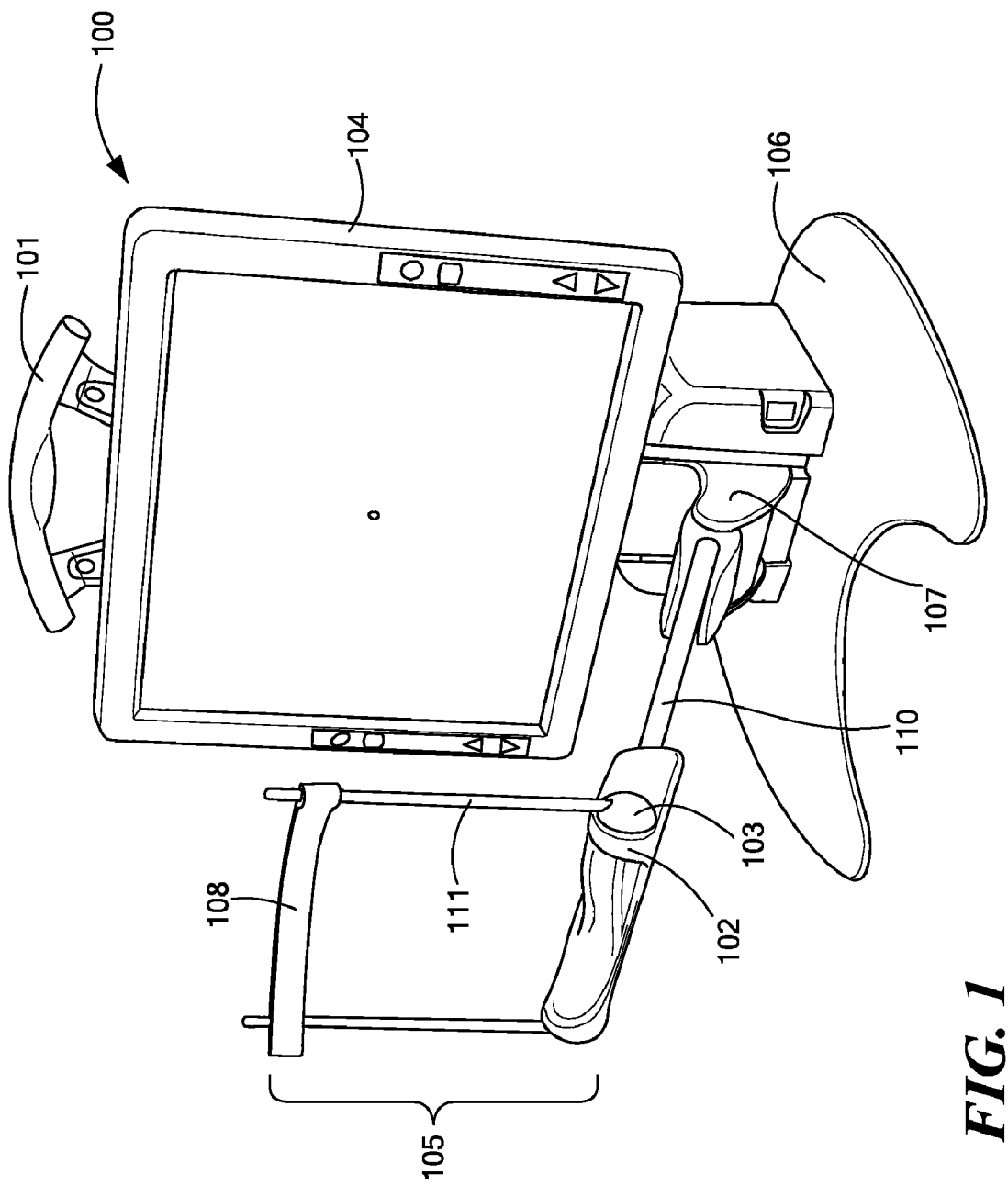
FIG. 1 is perspective view of a device according to an embodiment of the present invention.

FIG. 1. shows a front view of the vision restoration device 100. The device 100 is typically associated with a computer, which may be onboard (i.e., built-in), or attached via a cable or wireless connection. The computer contains a program for visual field testing or therapy; e.g., NovaVision VRT™ provided by NovaVision of Boca Raton, Fla. The computer may be, for example, a Microsoft Windows or Unix-based system, and may be a full personal computer or thin-client (e.g., a diskless Linux based thin-client). Responses of the subject to various stimuli are recorded to computer medium via an input device, which may be attached to the device 100, or to an external computer, either via a wire or cable or wirelessly.

The device 100 includes a head support assembly 105 that is used to position a subject's head in front of a computer display 104. The display 104 is supported on a base 106, and may be held above the base by a stem (item 250 of FIG. 2, below). By utilizing one or more articulations, the device 100 may be folded into a more compact form for storage and transportation. The head support assembly 105 is attached to an articulated arm 110 via a first folding articulation 103 that allows a forehead band 108 to fold onto the arm. The arm 110 is attached to the housing of the display 104 via a second articulation 107, and the junction between the base 106 and the stem 250 may also contain a third additional articulation (obscured in this view by a housing, but described below with reference to FIG. 2). The third articulation allows the display to be folded upon the base. A handle 101 allows the device to be easily carried, especially when folded; the handle may also include controls, e.g., for locking and unlocking the device for conversion between folded and unfolded modes.

The base 106 is designed to support the device and prevent it from toppling. Although the base 106 may take many forms, a U-shaped base minimizes weight, yet resists the downward force created when a subject rests their head in the head support assembly 105. This safety arrangement may make advantageously prevent unexpected forward tilting and toppling of the device 100. The base may be passive, or have built in circuitry and controls.

The computer display 104 is used to present stimuli (e.g. fixation and peripheral stimuli) to a subject. For maximum portability, the display may be a flat-panel type display, such as an LCD display (color or monochrome), although plasma displays or other types of displays may be equally well suited. The housing of the display 104 may include various controls; for example, buttons to control the elevation of the display, buttons to pause and resume operation of the testing or therapy. The display housing 104 may also contain an integrated microphone and/or video camera, which may be used as input devices for responding to displayed stimulus or to communicate with a remote clinical professional. Other input devices (not shown) for responding to displayed stimulus may also be associated with the display 104 or base 106; for example, a retractable mouse, or clipped-on wireless input device.

The display 104 may also include an antiglare feature such as an attachment points for a light-shielding hood (not shown), or an antiglare sensor system that notifies a subject or helper of the presence of excessive stray light. This antiglare sensor would ensure that the screen readability is not degraded to the point of affecting diagnostic or therapy. Should the sensor detect a glare condition exceeding a predetermined threshold, the device could halt or prevent the start of diagnostic or therapy activities until the detected glare is reduced or eliminated, e.g., by repositioning the device or by changing the ambient light conditions. For example, a camera, photodiode or other photosensor may be integrated into the head support assembly or the display to measure light impinging on or reflected from the surface of the display 104.

In some embodiments, the device 100 may include firmware, controls and an interface so that a second display (not shown), a keyboard (not shown), and a pointing device (e.g. a mouse, not shown) can be connected to it. These additional components allow a clinical professional to monitor or alter a diagnostic or therapeutic procedure. The information presented on the screen of the peripheral display can duplicate the screen 104 as seen by the subject (a mirror view). The clinical professional may also configure the computer to supplement or replace the mirror view with statistical data, graphs and other information related to the diagnostic or therapy underway. The clinical professional can use the keyboard or pointing device to modify the diagnostic or therapy sequence, insert comments to a therapy log associated with a computer-medium patient file, and make any other changes to the operating mode of the device 100.

In an embodiment, the head support assembly 105 has a chinrest 102, and a forehead band 108 supported by two posts 111. In use, a subject will rest their chin upon the chinrest 102, and their forehead against the forehead band 108. The chinrest 102 and forehead band 105 may be curved to increase comfort and ensure reproducible alignment. The head support assembly 105 may be folded onto the arm 110 prior to transport and storage. For example, the assembly may rotate around an axis defined by the first articulation 103. If the arm 110 is also foldable against the display, then the overall volume defined by the folded device 100 will be lower if the head support assembly 105 folds outwardly, i.e., rotates away from the display 104. In this case, a limit (not shown) may prevent the head support assembly 105 from rotating past an upright position, yet allow folding backward for storage. Optionally, a locking mechanism may be included to lock the head support assembly 105 in an extended and/or folded position.

In an embodiment, the elevation of the chinrest 102 with respect to the center of the screen of the display 104 is fixed and not adjustable. This elevation is chosen such that once the chin of a patient is positioned within the chin rest, the eyes of this patient are in line with the center of the screen with a maximum vertical error of +/−3.00 inches.

In another embodiment, the distance from the chin to the surface of the flat screen may also be fixed and not adjustable. This fixed distance has a value between 5 inches and 20 inches. The choice of this fixed distance is based on the width of the image presented on the screen and the desire to achieve a lateral field of view angle for each eye of between about 30 degrees and 60 degrees, depending on diagnostic and therapy objectives.

To effect therapy specific to a particular lateral portion of the visual field, it may be advantageous to offset the subject's head laterally in relation to the display. Accordingly, in an embodiment, the head support assembly 105 may contain a mechanism to allow lateral repositioning of the head support assembly 105 relative to the display 104. The mechanism may utilize a trigger to release an articulating mechanism at the base of the arm 110. Release may be effected via, for example, a cable, or via a cable attached to a solenoid locking mechanism associated with the second articulating mechanism 107 at the base of the arm. Such actuation controls may be located on the head support assembly 105. The left or right lateral adjustment may be limited, e.g., to an offset of between about 1 to 4 inches. Alternately, head support assembly 105 may be laterally positioned by sliding the assembly 105 along a track, or with a lead screw mechanism.

The head support assembly 105 may optionally include sensors (not shown) that detect the presence or absence of the subject's head. During unattended stimulation procedures, it may be difficult to ascertain whether the subject remains consistently positioned with their chin located within the chinrest 102. For example, the subject could move or take a brief break while continuing actuation of the input device. In addition, the subject's head may be misaligned. As a result, spurious negative data may be accumulated. In an embodiment, one or more detectors may be placed within the chinrest 102, or other location, to detect the chin of the subject, and may detect proper alignment of the chin and/or forehead of the subject. In the event that these detectors sense that the subject's chin is no longer properly within the head support assembly 105, compensatory action may be taken. Examples of compensatory actions include testing or therapy may be automatically paused, annotating an associated patient therapy file, ignoring data from a time period, repeating part of the procedure, or combination thereof. As a result, accumulation of spurious data from a non-present subject is prevented. If paused, the procedure may be automatically resumed when the detectors sense that the subject's chin is has returned to the chinrest, or manually resumed once the patient restarts the therapy by pressing on an input device keys. Those skilled in the art know that multiple forms of detectors could be used for this purpose including: optical detectors, (e.g., visible and infrared light detectors), thermal sensors, ultrasonic detectors, pressure detectors within the chin rest, force sensors, strain gauges, and conductance sensors, to name a few.

Figure 2:
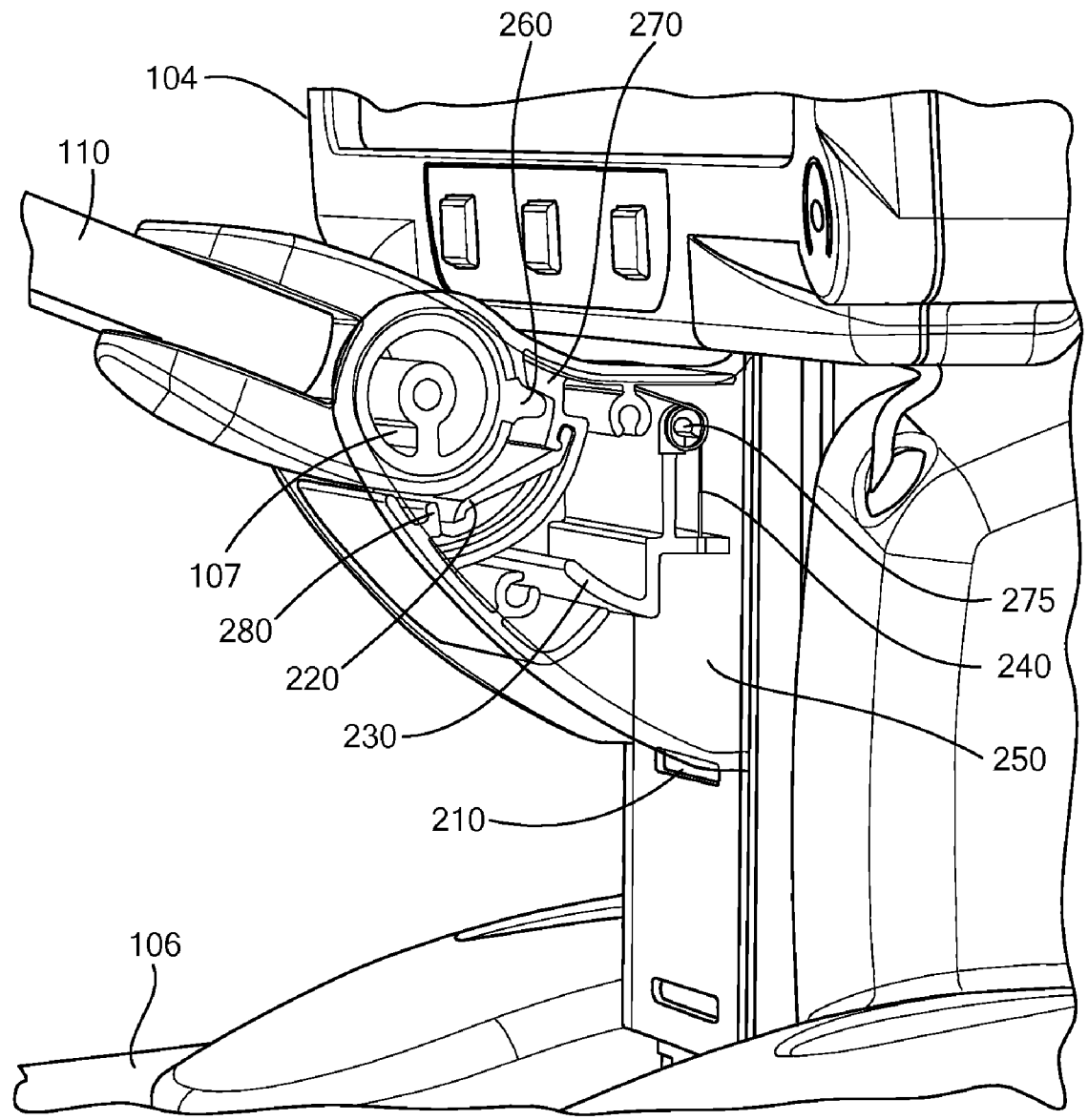
FIG. 2 shows a cut-away side-view of how the chinrest arm may be coupled to the drive mechanism.

As shown in FIG. 2, the chin rest arm 110 has a second articulation (hinge 107) at its base (i.e., near the intersection of the arm 110 and housing of the display 104) which allows this arm to be folded vertically against the display 104 to make the entire device simpler to package and transport. In the unfolded position, a tab 260 abuts an unfolded-mode limit 270 to define the fully extended position and support the levered weight of the subject's head. In the folded mode, a locking spring 220 applies force to the tab 260 and presses it against a folded-mode limit 280.

To compensate for the height of the subject and or the distance between their eyes and chin, the arm 110 and hinge 103 may be together slidably positionable along the height of the stem 250. A spring-loaded handle 240, has a tab that extend into a slot 210 in the stem 250 to secure the arm 110 elevation in one of multiple pre-defined positions. The positions of the slots 210 may be chosen to correspond to a given distribution of eye to chin distances of the population (e.g., to cover 3 standard deviations of distances as determined from the analytical data contained in Baidai. et. al., "Relationship between Anthropometric and Cephalometric Measurements and Proportions of the Face of Healthy Young White Adult Men and Women,"J. of Craniofacial Surgery 14(2): 154-161, March 2003). To unlock and reposition the arm 110, a user pulls the handle 230 to rotate the handle 230 around a handle hinge 275 and disengage the tab of the handle 230 from a slot 210. The user then releases the handle 230 and raises or lowers the handle 210; a handle spring 240 will force the re-engagement of the tab into a new slot.

Figure 3:
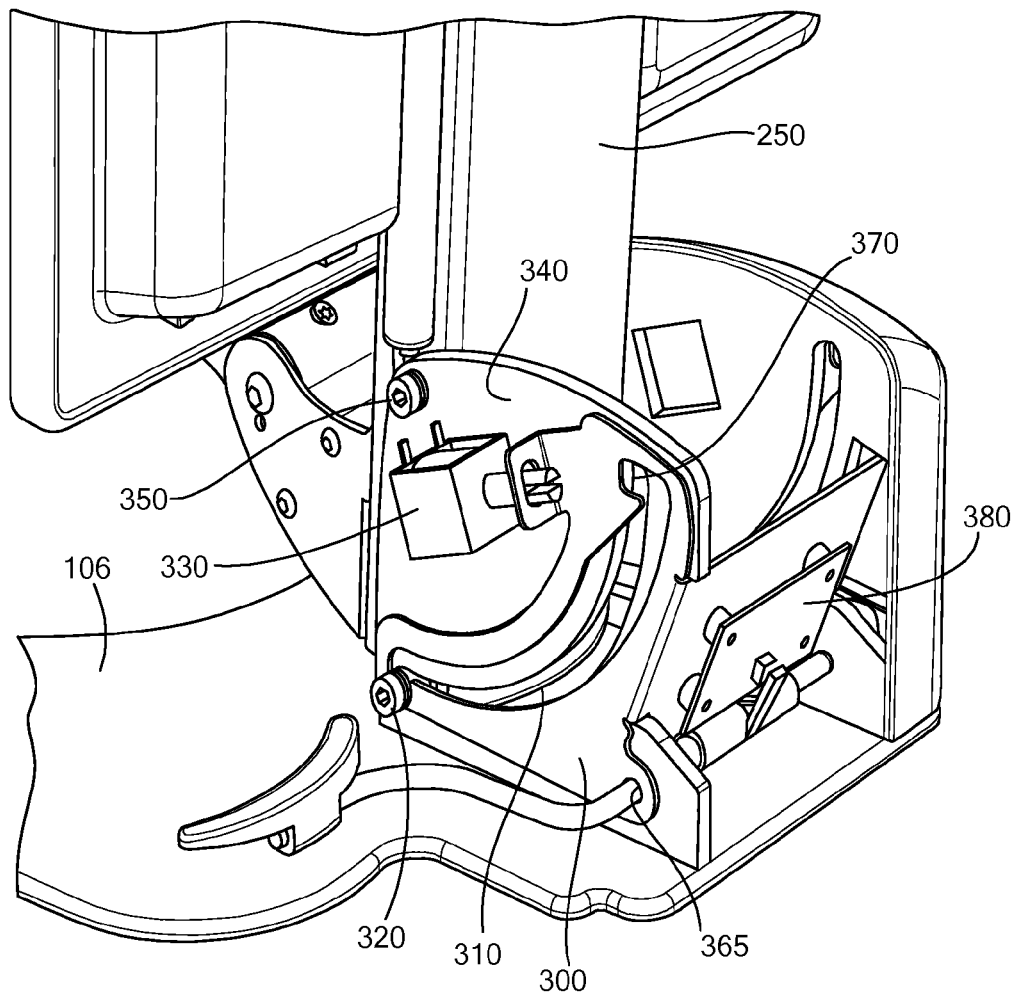
FIG. 3 shows one example of how the drive mechanism may be coupled to the base of the device with a folding mechanism.

FIG. 3 shows the third articulation that allows folding of the display 104 relative the base 106. The stem 250 (and attached display 104) may be rotated around a third articulation hinge 350. Pivot plates 340 are attached via the hinge 350 to either side of the stem 250 and are also attached to the base 106. A shoulder screw 320 travels in a pivot groove 310 within at least one pivot plate 300. At least one grooved pivot latching plate 300 is used to secure the stem 250 in either the folded or the unfolded position. The latching plate 300 pivots on a pivot latch hinge 365, and has a central groove with two terminal notches 370 designed to accommodate a shoulder screw 320 attached to the bottom of the stem 250. A solenoid actuator 330 rotates the latching plate 300 about the hinge 365 axis to engage the shoulder screw 320 in the notch 370, thereby locking the device. A passive biasing mechanism may also be used to bias the latching plate 300 toward a locking position so the device 100 will remain locked when folded or unfolded but not powered. For example, a latching spring (not shown) may connect the pivot plate 340 to the latching plate 300 to exert an upward bias on the plate 300.

In some embodiments, the device 100 may be folded at more than one of the first, second and third articulations to make it more compact for ease of transportation. For instance, a folding sequence may include:

Folding the forehead band assembly 108 down on the chinrest arm 110,
Folding the arm 110 against the display,
Activating an unlocking mechanism to allow the head support assembly 105 to be folded against the base 106 of the device, and folding the device 100 in this way.

Figure 4:
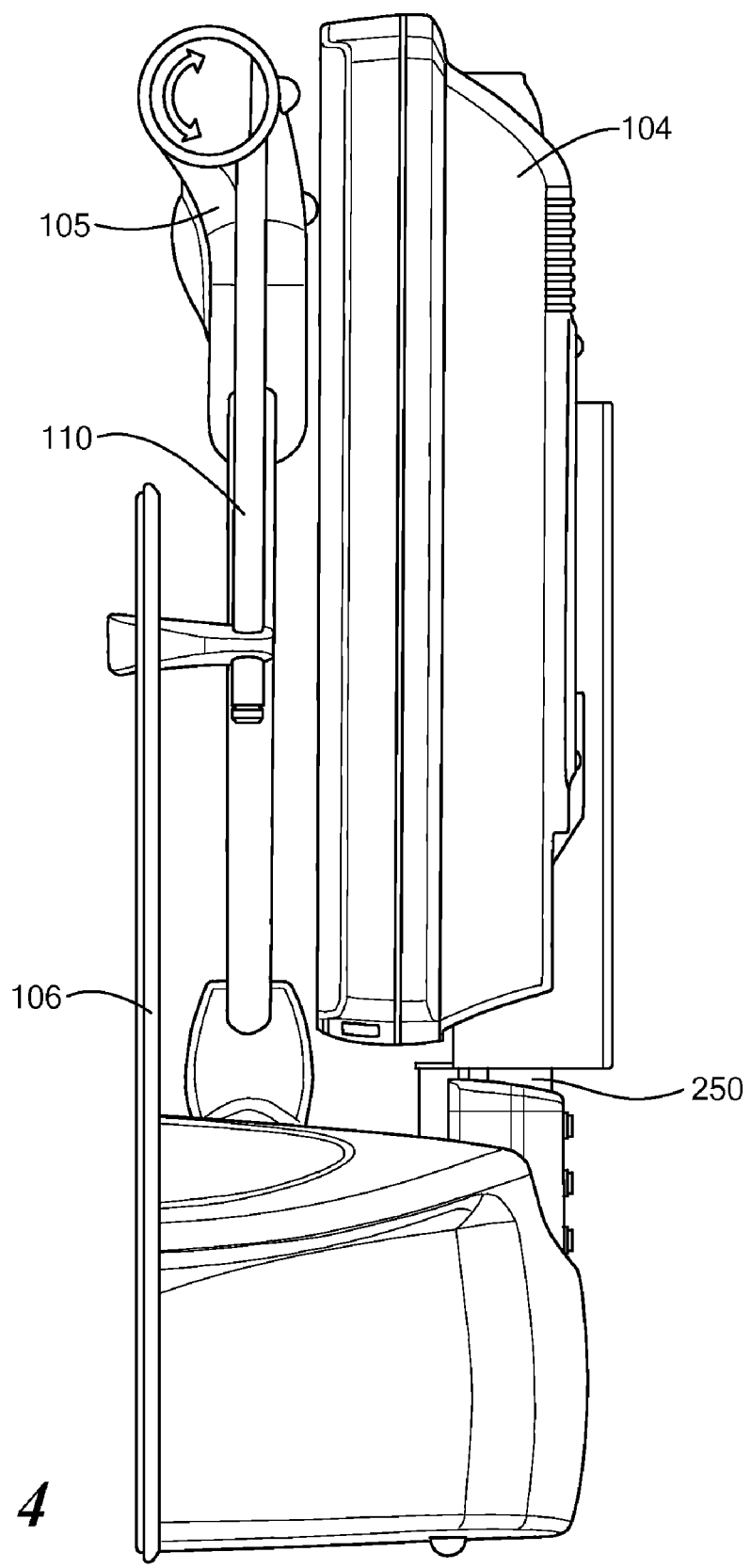
FIG. 4 shows a side view of an embodiment of the device in a folded configuration.

FIG. 4 shows the device 100 in a folded configuration. After folding, the device 100 may be packed for shipping. Using the reverse sequence, the device 100 may then be unfolded for use. The device 100 may lock in the unfolded and folded state. Actuation of the lock may be triggered via a control; for example, a button on the handle 101. The button may, for example, actuate one or more locking/unlocking solenoids.

In a related embodiment, as a safety feature, the chinrest arm 110 folding articulation 107 may collapse toward the base 106 in response an excessive downward vertical load applied to the chin rest. This safety feature prevents the toppling-over of the entire device when an excessive load is applied to the chin rest. For example, a clutch mechanism can be factory preset to any load exceeding a threshold of between 1.0 lb. and 200 lb. Upon collapse of the chinrest arm, it is possible for the patient to reposition the arm in its preset position by simply lifting the arm and re-engaging the clutch mechanism.

To maximize patient comfort, the display 104 and head support assembly 105 may be elevated or lowered vertically, to bring the chinrest 102 to the elevation suitable to provide each patient with maximum comfort during use of the device 100.

Figure 5:
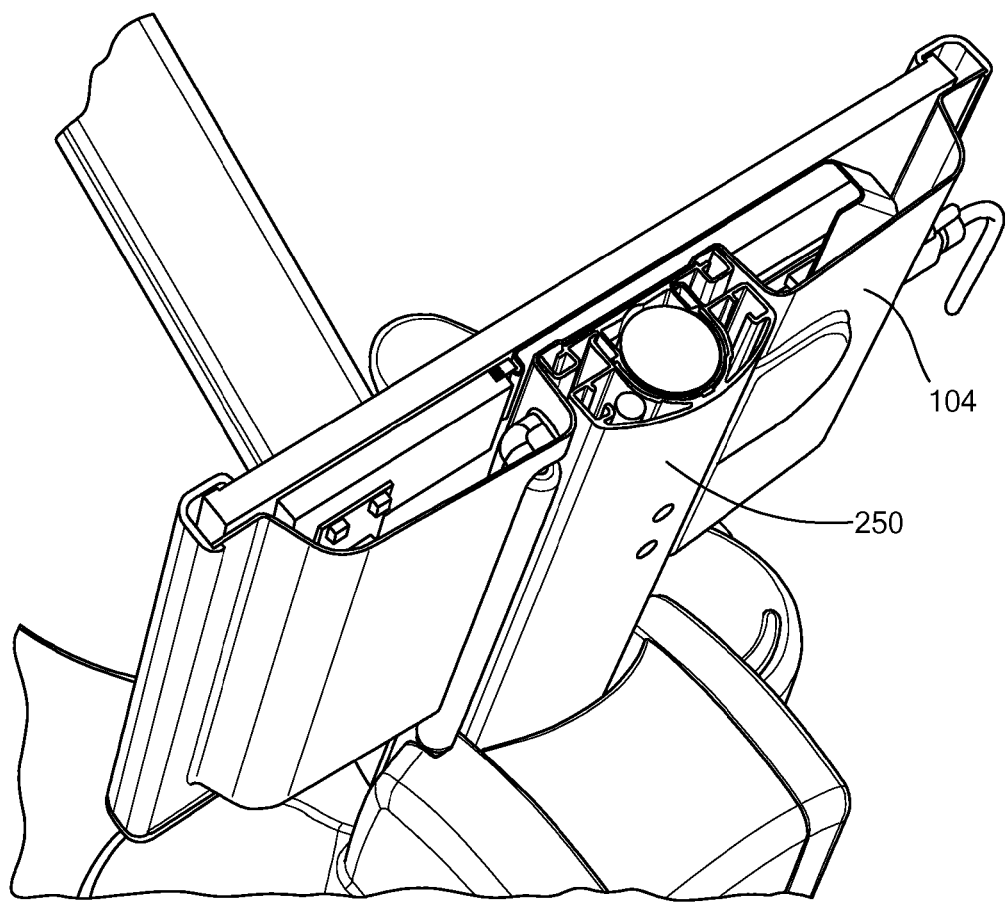
FIG. 5 shows a top perspective cut-away view of an embodiment of the device having an electromechanical drive for adjustment of the display elevation.
Figure 6:
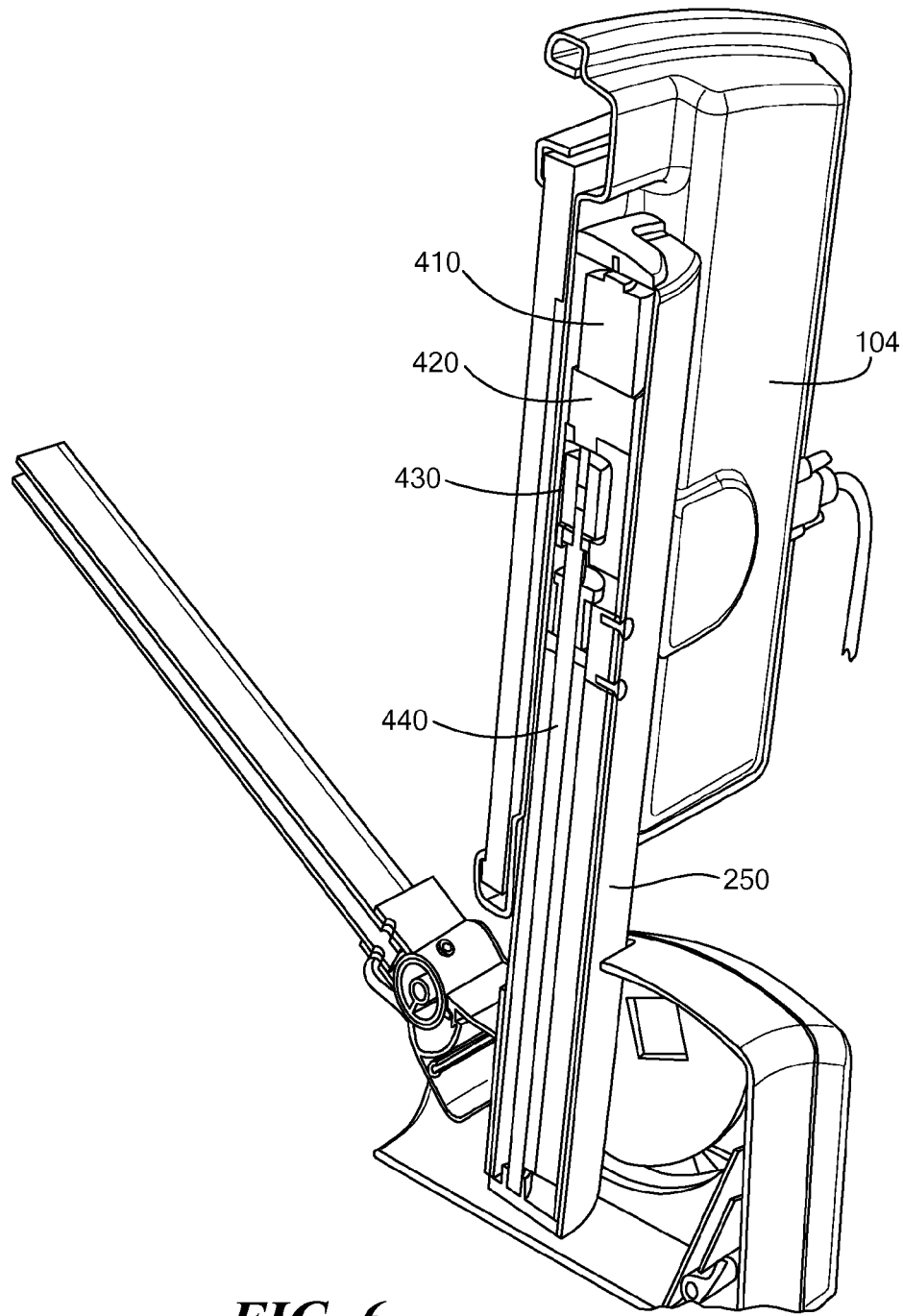
FIG. 6 shows a side perspective cut-away view of the embodiment of FIG. 5.

The device 100 may be manually adjustable or may include one or more motorized parts for automatic positional adjustment. FIGS. 5-6 show a device 100 that adjusts the elevation of the display 104 automatically, by driving the display 104 vertically up or down along the length of the stem 250. In this embodiment, the combined display 104 and head support assembly 105 may be simultaneously elevated or lowered using a drive mechanism contained within the device 100, while maintaining their elevation in relation to each other. This drive mechanism may be controlled by the subject using [up] and [down] controls which may be located for example on the base 106, or around the screen of the display 104 or on other locations of the device 100. For instance, the elevation controls could be located on the head support assembly 105; they could also be wireless remote controls, or other input devices. This screen elevation control may also be speech-actuated by the patient.

The drive mechanism includes a leadscrew 440/drive nut 430 mechanism powered by a DC motor 410 with a gearbox reduction 420. A current sensor may be placed in the circuit powering the DC motor to sense the end-of travel of the drive mechanism in either direction. When a stall condition occurs (end-of travel) the resulting increased motor current is detected and the energy supplied to the motor in that direction is terminated. The rotation speed of the motor may be monitored so that the amount of energy supplied to the motor is automatically adjusted (i.e. pulsed width modulation) to achieve a similar speed when the display 104 and head support assembly 105 is traveling upward or downward. There is an increased load on the motor assembly when the display/chin rest assembly travels upward than downward so the speed detector and resulting energy adjustments operate as load-compensator.

As a safety feature, if the display/chin rest assembly 105 encounters an interference (e.g., a human limb between the display 104 and base 106 of device 100) when the display 104 and head support assembly 105 travel downward, the DC motor current will increase and the motor rotation speed will decrease and may diminish to zero. Detection of either or both conditions will result in stoppage of the motor, and may be followed by an immediate displacement of the drive mechanism in the opposite direction for a distance sufficient to relieve pressure on the interference and allow its removal. Those skilled in the art know that a DC motor/gearbox/leadscrew/drive nut implementation for the device 100 is only one possible implementation among many; a rack and pinion, pneumatic, hydraulic, solenoid and ratchet system or linear motor, among others, could be used for the drive mechanism of the device 100.

Embodiments of the present invention may include one or more of the following drive features:

A drive mechanism which moves the display laterally (to the left or to the right). This lateral drive mechanism for the display could be actuated manually, or via electromechanical controls.

Separate drive mechanisms for the head support assembly 105 and for the display 104 may allow for the spatial relationship between the head support assembly 105 and the display 104 to be adjusted independently.

In a related embodiment, the device 100 may automatically set the relationship between the chinrest 102 and the display 104. For example, a patient could adjust the chinrest position manually or electromechanically and the display 104, equipped with an eye tracker system, automatically brings the center of the screen exactly in line with the eyes of the patient for any position of the chin rest. Accordingly, the device 100 will automatically compensate for patient-to-patient variability in eye to chin distance.

In a clinic, setting the same device 100 may be used by multiple patients each day and it may save time to record the spatial location of the chinrest 102 and of the display 104 in a memory device that is specific to each patient. After completing the initial adjustments of chin rest and screen during initial diagnostic or therapy, the spatial coordinates may be automatically stored in the memory of the MSD (memory Storage Device) specific to the patient, along with the therapy profile and patient identification information already present in this MSD. The next time the patient uses a device 100 (the same device or other device of the same type) the device may read the spatial coordinates from the patient MSD, and will automatically pre-position the chinrest and screen as soon as the MSD is inserted in the VRT device. Upon completion of this pre-positioning, the patient can still fine-tune these adjustments using [up] and [down] manual controls at his disposal to reflect a different chair or seating position. Alternatively, the stored positional information may be used to aid in manual adjustment of the device.

If positional corrections are made, the revised spatial coordinates of the chin rest and screen are updated in the MSD. The expression "memory storage device" (MSD) used herein should be taken broadly and is not intended to describe solely storage devices making use of the USB port (or other ports) found on most computers. In some embodiments of this invention, the patient storage device may take forms other than MSD such as "wallet card with a built in computer." An MSD may be any storage device containing patient specific data, whether this devices needs to be physically connected to the device for its data to be used by the device, or whether this patient-specific storage device can communicate wirelessly and bi-directionally with the VRT device using techniques such as RFID.

This chinrest position and therapy information can also be stored in the memory of the device itself 100 and can be retrieved, along with therapy data by entering a subject identifier code. For example, the subject identifier code may be input using an input device, including a biometric identification system, e.g., a fingerprint or retinal scanner.

In another embodiment, the chinrest position and therapy information can be stored on a remote computer server, and could be retrieved from any device using its internet access upon entry by the patient of a specific I.D. or upon presentation of a proper biometric identifier such as the tip of a finger placed on a fingerprint scanner located on the device 100 or coupled to the device 100.

The device 100 may be designed to be connected to the internet using a phone connection (dial-up), or wide-band high speed connection (e.g., Ethernet, cable, DSL, 3G, or WiMax). For instance, the device could include an internal modem. This internet connection can be used for the following purposes:

To transfer patient diagnostic and/or therapy data to a remote database (upload).

To transfer new operating software, diagnostics or therapeutic profiles to the device 100 (download).

To automatically notify a remote location when the device 100 detects that a particular therapeutic profile is not followed by a patient (patient compliance), or when the patient condition or response appears to be deteriorating.

To allow a subject or user to contact a clinical professional and request assistance or guidance.

Using technology such as VoIP (Voice over Internet Protocol), the patient and the clinical professional located at a remote site can talk to each other. During this process, a live picture of the clinical professional can be presented on the screen or a portion of the screen (Picture in Picture). A microphone and speaker placed in the device 100 support audio communications. Once this remote mode is activated, and in order to allow the clinical professional to better assist the patient, the remotely located clinical professional can view on his/her own screen the same screen data seen by the patient; this patient screen data can also be supplemented by or completely replaced by statistical data, historical data, medical data, graphs and other information related to the specific patient being treated and to the diagnostic or the therapy underway.

In some embodiments, one or more input devices may be provided for the patient to indicate that they have observed a visual stimulus on the screen. The base plate 106 of the device 100 may be equipped with an input device on each side. These input devices can be equipped with one up to ten pushbutton switches. A wired or wireless input device can also be used as an alternative to the base plate input devices. The above mentioned input devices are all coupled to the computer of the device 100 and can be used concurrently and simultaneously if desired and in any combination. A variety of other input device types may be used; for example, a mouth-actuated switch (e.g., blowing air in a tube to actuate a pressure sensitive switch), a microphone, a finger actuated switch, a foot actuated switch, a joystick, a mouse, a trackpad, a trackball, and an accelerometer-based device. The device 100 is capable of recording to memory locally or remotely (e.g., via internet link) which input device (type and specific identifier code) was used for a specific therapy or diagnostic.

An input device coupled to the computer of the device 100 may also be equipped with a pause button to allow a subject to interrupt the therapy when necessary, and then to resume this therapy by pushing the pause button once more, or if desired, by pressing any other key on one of the input device. During a pause, the display 104 can present a message reminding the patient that the therapy has been paused and that she needs to take a specific action to either resume or terminate the therapy.

In alternative embodiments, the disclosed methods for relative positioning of a subject and a display may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The described embodiments of the invention are intended to be merely exemplary and numerous variations and modifications will be apparent to those skilled in the art. All such variations and modifications are intended to be within the scope of the present invention as defined in the appended claims.

The invention claimed is:

1. An adjustable device for treatment of a neurological vision deficit of a subject, diagnostic testing of a visual field of a subject, or both treatment and testing of a subject, the subject having both a head and an eye, the adjustable device comprising:

a base;

a computer display, mounted on the base, characterized by an elevation with respect to the base and adapted to present visual stimuli to the subject;

a head support assembly including a chinrest characterized by an elevation with respect to the base and a lateral position, the chinrest adapted to support and position the head of the subject with respect to the display and adapted to resist a downward force of the head of the subject; and an articulated arm joining the base and the head support assembly in such a manner as to permit folding of the head support assembly toward the display and wherein the display is joined to the base in such a manner as to permit folding of the display toward the base, whereby the device is foldable for creating a compact and portable device.

2. A device in accordance with claim 1, wherein the elevation of the chinrest relative to the elevation of the display is adjustable.

3. A device in accordance with claim 1, wherein the elevation of the chinrest with respect to the display, and the elevation of the display with respect to the base, are adjustable.

4. A device in accordance with claim 1, wherein the lateral position of the chinrest is adjustable.

5. A device in accordance with claim 1, further comprising an eye-tracker adapted to track a position of the subject's eye and a processor for adjusting the relative position of the chinrest and the display on the basis, at least, of the position of the subject's eye.

6. A device in accordance with claim 1, further comprising a motorized positioning system adapted to electromechanically adjust at least one of the elevation and lateral position of the chinrest relative to the display.

7. A device in accordance with claim 1, further comprising a motorized positioning system adapted to electromechanically adjust the elevation of the chinrest and the display relative to the base.

8. A device in accordance with claim 1, further comprising a memory storage device for storing and recalling positional settings associated with a given subject.

9. A device in accordance with claim 8 further comprising a motorized positioning system that electromechanically adjusts the device in such a manner as to reproduce stored positional settings.

10. A device in accordance with claim 1, wherein the device is adapted to be locked in one of a folded and an unfolded position.

11. A device in accordance with claim 1, wherein the chinrest is adapted to support the head of the subject up to a threshold of supporting upward force and wherein the chinrest is further adapted such that downward force in excess of the threshold causes a downward collapse of the chinrest.

12. A device according to claim 11, wherein the threshold is chosen to discourage the toppling of device.

13. A device according to claim 1, further comprising a handle attached to the display.

14. A device according to claim 1, further comprising a computer, operably coupled to the device, adapted to direct a presentation of stimuli upon the display, and further adapted to record user responses to those stimuli.

15. A device according to claim 14, wherein the computer is one of an onboard integrated computer, a computer coupled by a cable, and a computer coupled by wireless communication.

16. A device according to claim 14, wherein the head support assembly includes a sensor, operatively coupled to the computer, and adapted to detect the presence of the head of the subject.

17. A device according to claim 16, wherein the sensed absence or presence of the head prevents the accumulation of spurious data from a non-present subject.

18. A device according to claim 14, further including a stimulus recording input device selected from the group consisting of a mouth-actuated switch, a microphone, a finger actuated switch, a foot actuated switch, a joystick, a mouse, a trackpad, a trackball, and an accelerometer-based device.

19. An adjustable device for the treatment of a neurological vision deficit, the diagnostic testing, or both the treatment and testing of a subject having a head the device comprising:
means for displaying visual stimuli to the subject;
a head support means for positioning, in an extended position, the head of the subject in relation to the display; and
an articulated arm joining a base and the head support means in such a manner as to permit folding of the head support means toward the display means and wherein the display means is joined to the base in such a manner as to permit folding of the display means toward the base, whereby the device is foldable for creating a compact and portable device.

20. A device according to claim 19, further comprising means for inputting a user response to the stimuli.

21. A device according to claim 19, wherein a excessive downward force, sufficient to topple the device, causes a collapsing means to yield, thus preventing the toppling of the device.

22. A device according to claim 19, further comprising motive means for positioning the head of the subject relative to the display means.

23. A device according to claim 19, further comprising motive means for positioning the absolute elevation of the display means and head support means.

24. A device according to claim 19, further comprising means for storing and recalling positional setting of the device.

25. A device according to claim 19, further comprising means for tracking the position of a subject's eye and using the eye position to adjust the configuration of the device.

26. A device according to claim 19, further including a head position sensing means, wherein the sensed misalignment or absence of the head prevents the accumulation of spurious data from a non-present subject.

27. A device for administering vision therapy and/or diagnostic testing procedures, the device comprising:
a display foldably connected to a base, and a head support assembly foldably connected via an articulated arm.

28. A device in accordance with claim 27, wherein the head support assembly is foldably connected to arm.

29. A device in accordance with claim 27, wherein the device is lockable in a folded state.

30. A device in accordance with claim 27, wherein the device is lockable in an unfolded state.

31. A device in accordance with claim 29 further comprising an actuator for locking and unlocking the device.

32. A device in accordance with claim 30 further comprising an actuator for locking and unlocking the device.

* * * * *